United States Patent [19]

Yamamoto

[11] Patent Number: 5,687,428
[45] Date of Patent: Nov. 18, 1997

[54] GOGGLES

[75] Inventor: Tamenobu Yamamoto, Higashi-Osaka, Japan

[73] Assignee: Yamamoto Kogaku Co., Ltd., Higashi-Osaka, Japan

[21] Appl. No.: 608,438

[22] Filed: Feb. 28, 1996

[30] Foreign Application Priority Data

Mar. 23, 1995 [JP] Japan .................... 7-064459

[51] Int. Cl.⁶ .................................. A61F 9/02
[52] U.S. Cl. ........................... 2/445; 351/128
[58] Field of Search .................. 2/445, 446, 428, 2/430, 440, 452; 351/128, 124, 126, 133

[56] References Cited

U.S. PATENT DOCUMENTS

| | | | |
|---|---|---|---|
| 1,923,566 | 8/1933 | Baker | 351/128 |
| 4,162,542 | 7/1979 | Frank | 2/446 X |
| 4,279,039 | 7/1981 | Drew | 2/428 |
| 4,468,819 | 9/1984 | Ohno | 2/430 |
| 5,459,882 | 10/1995 | Yamamoto | |
| 5,502,844 | 4/1996 | Alvarado | 2/428 X |
| 5,515,551 | 5/1996 | Yashiro | 2/445 X |
| 5,546,611 | 8/1996 | Lathrop | 2/428 |

FOREIGN PATENT DOCUMENTS

| | | | |
|---|---|---|---|
| 1 36505 | 11/1989 | Japan . | |
| 1251961 | 11/1971 | United Kingdom | 351/128 |

*Primary Examiner*—Peter Nerbun
*Attorney, Agent, or Firm*—Oblon, Spivak, McClelland, Maier & Neustadt, P.C.

[57] ABSTRACT

The present invention relates to goggles for use in swimming, skiing, motorcycling and other activities. The goggles comprise a pair of right and left eyecups, a connecting member interconnecting opposing inner ends of the eyecups, and an elastic band having opposite ends each connected to an outer end of each of the eyecups, wherein the eyecups are each provided with a mount portion which defines a plurality of engagement holes aligned longitudinally of the eyecups, and the connecting member is removably fitted into one of the plurality of engagement holes of each mount portion.

7 Claims, 4 Drawing Sheets

GOGGLES

BACKGROUND OF THE INVENTION

The present invention relates to goggles for use in swimming, skiing, motorcycling and other activities.

An example of conventional goggles for swimming is disclosed in U.S. Pat. No. 4,468,819.

The conventional goggles comprise a pair of right and left eyecups, a flexible connecting member and an elastic band. Each of the eyecups is provided, at its nasal or inner end, with a mount portion to be connected to the connecting member, the mount portion having a single hole for engagement with the connecting member.

The connecting member is provided with a plurality of protuberances at opposite longitudinal ends thereof, so that the distance between the eyecups can be adjusted by selectively engaging a protuberance of the connecting member with the engagement hole.

Another example of conventional goggles is disclosed in Japanese Utility Model Publication No. Hei 1-36505. The goggles of this publication include a connecting member provided with a plurality of through-holes at opposite longitudinal ends thereof, so that the distance between the eyecups can be adjusted by selecting one of the through-holes of the connecting member and fittedly inserting a securing member through the selected through-hole and an engagement hole.

In the goggles disclosed in aforementioned references, the distance between eyecups can be adjusted by selecting a protuberance or a through-hole of the connecting member depending on the size of a wearing portion of a user, so that the goggles can comfortably fit the head of the user. In the goggles disclosed in U.S. Pat. No. 4,468,819, however, since the connecting member has flexibility and a U-shaped form, the eyecups are drawn away from each other with the connecting member drawn in opposite directions by the elastic band when the goggles are worn by the user. As a result, even though the distance between the eyecups are adjusted for an individual user, the distance is varied once the goggles are fitted around user's head, causing a problem of deteriorated fit of the eyecups to the face of the user. Further, the adjustment of the distance after the wearing of the goggles is cumbersome.

The goggles disclosed in Japanese Utility Model Publication No. Hei 1-36505 have some inconveniences in adjustment that the securing member is required to be fitted into the through-hole of the connecting member and the engagement hole of each eyecup and that when the goggles are to be worn by a child, outer end portions of the connecting member, which become unusable, must be cut off.

SUMMARY OF THE INVENTION

In view of the foregoing, it is an object of the present invention to provide goggles which allow a ready adjustment of the distance between the eyecups thereof and provide an improved fit to the face of a user after the adjustment of such distance.

Goggles of the present invention incorporates the following technical improvements so as to achieve the aforementioned object.

Goggles according to the invention comprise a pair of right and left eyecups, a connecting member interconnecting opposing inner ends of the eyecups, and an elastic band having opposite ends each connected to an outer end of each of the eyecups, wherein the eyecups are each provided with a mount portion which defines a plurality of engagement holes aligned longitudinally of the eyecups, and the connecting member is removably attached to one of the engagement holes of each mount portion selectively.

The eyecups each comprise a lens portion and a peripheral wall rearwardly extending from the peripheral edge of the lens portion. The mount portion projects from the peripheral wall substantially parallel to the lens portion and has a front side comprising a flat surface defining the engagement holes in the form of vertically elongated slots.

The connecting member is of a rectangular shape transversely elongated in a front view of the goggles and has a rear side formed with a recess in a longitudinally central portion thereof and contact surfaces on opposite sides of the recess which closely contact the corresponding flat surfaces of the eyecups. The contact surfaces are each formed with an engaging claw protruding rearwardly therefrom and removably inserted into one of the engagement holes.

The engaging claw has an engaging protuberance on a tip portion thereof which hooks a peripheral edge of the engagement hole. The engaging claw has a base portion having substantially the same cross sectional configuration as the engagement hole and closely fitted into the hole. The engaging protuberance is formed by offsetting the axis of the tip portion of the claw with respect to that of the base portion of the claw. The engaging claw is elastically deformable.

The goggles according to the present invention can be readily and quickly fitted to the face of a user by appropriately selecting one of the engagement holes of each eyecup depending on the size of the wearing portion of the user and fittedly engaging the engaging claw formed at each of the opposite ends of the connecting member with the selected one of the engagement holes to interconnect the right and left eyecups with the distance therebetween properly adjusted.

Further, the goggles of the invention allows even a child to adjust the distance between the eyecups by means of the connecting member very easily and provides an improved fit to the face of the user after the adjustment. Additionally, the goggles of the invention eliminate a possible need of cutting off outer end portions of the connecting member and exhibit improved appearance with no possibility of deteriorating their fit onto user's face because of the outer end portions of the connecting member propping up the eyecups.

The foregoing and other objects, features and attendant advantages of the present invention will become apparent from the following detailed description.

DESCRIPTION OF THE PREFERRED EMBODIMENTS

The present invention will now be described in detail by way of embodiments shown in the accompanying drawings.

Figure 1:
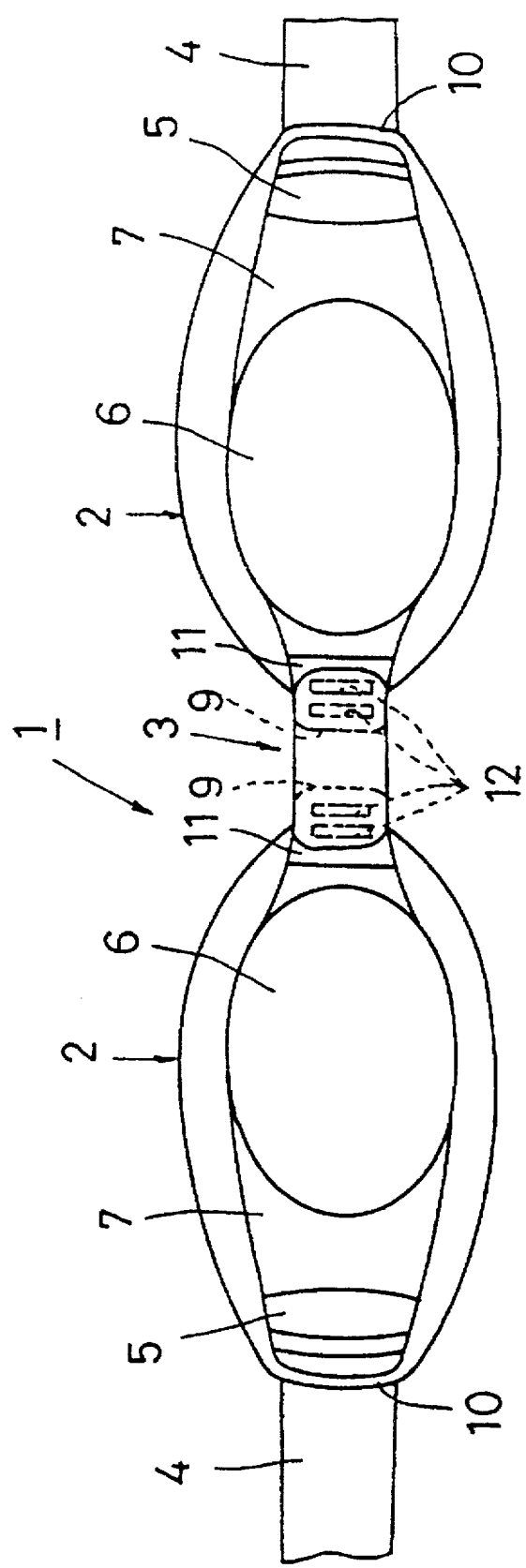
FIG. 1 is a partially cutaway front view showing an embodiment of the present invention.
Figure 2:
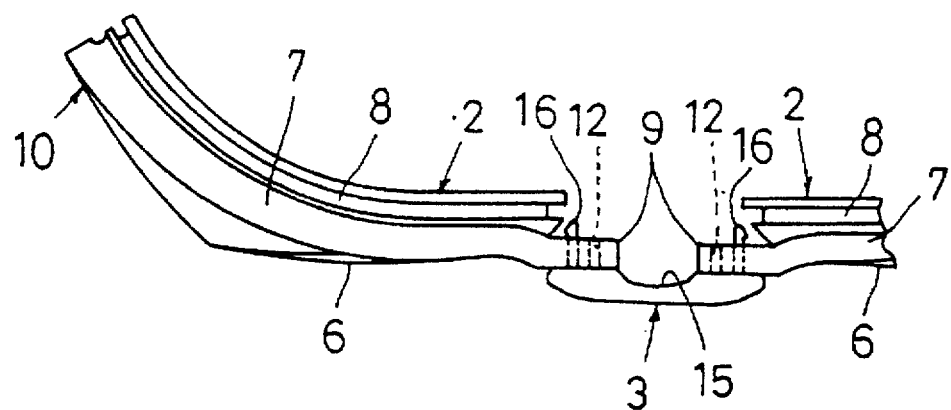
FIG. 2 is a partially cutaway top plan view showing the embodiment.
Figure 3:
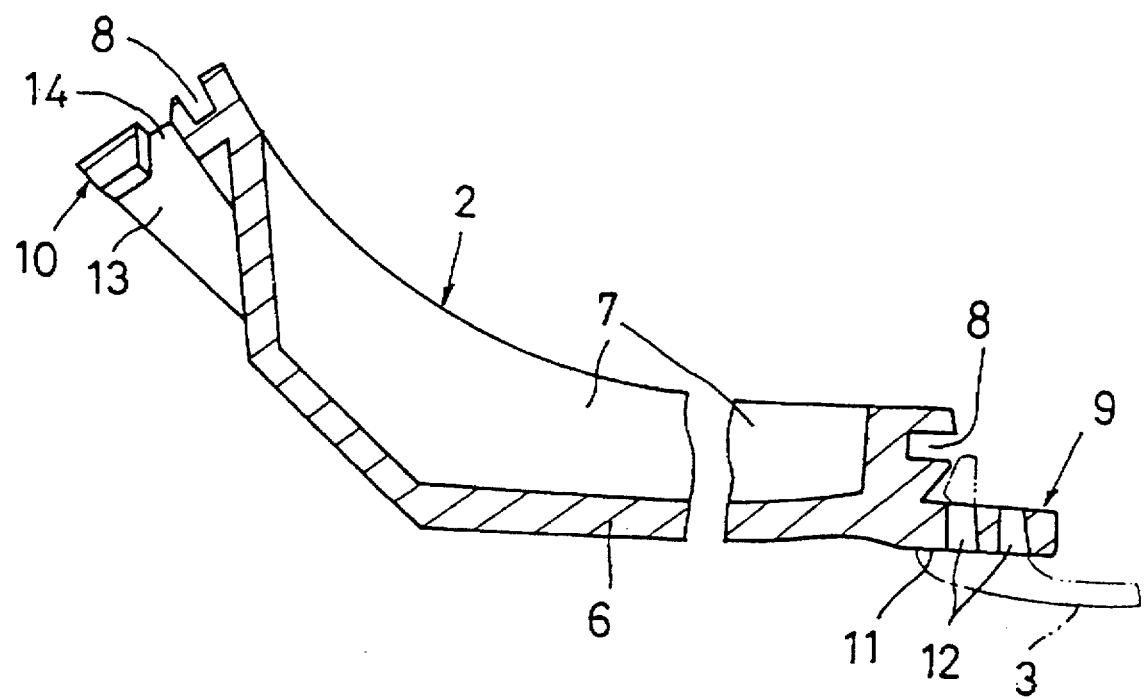
FIG. 3 is an enlarged transverse sectional view of an eyecup of the embodiment.
Figure 4:
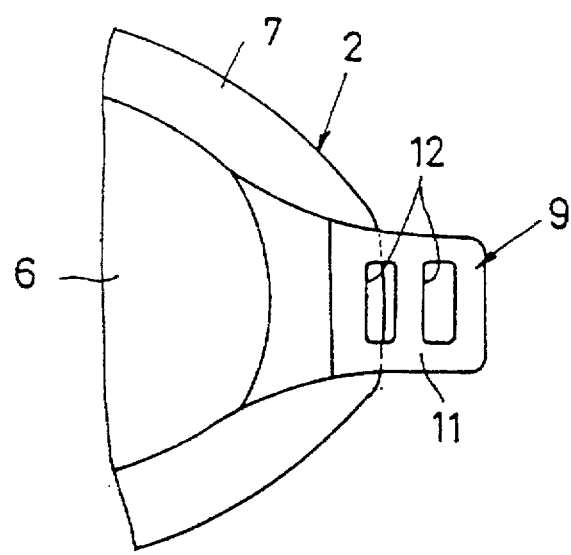
FIG. 4 is an enlarged fragmentary front view of the embodiment.
Figure 5:
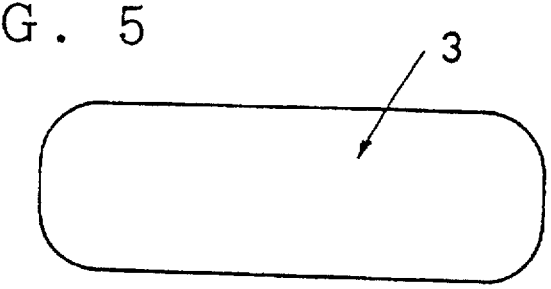
FIG. 5 is a front view of a connecting member of the embodiment.
Figure 6:
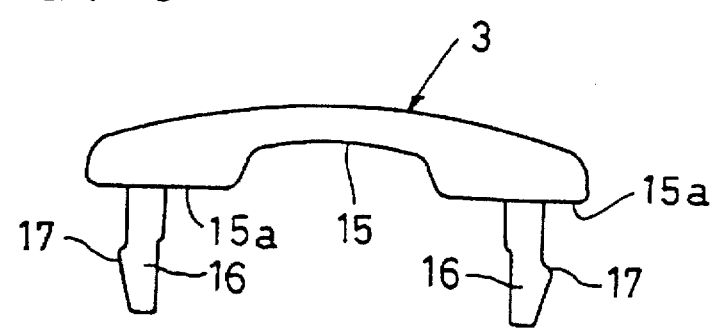
FIG. 6 is a top plan view of FIG. 5.
Figure 7:
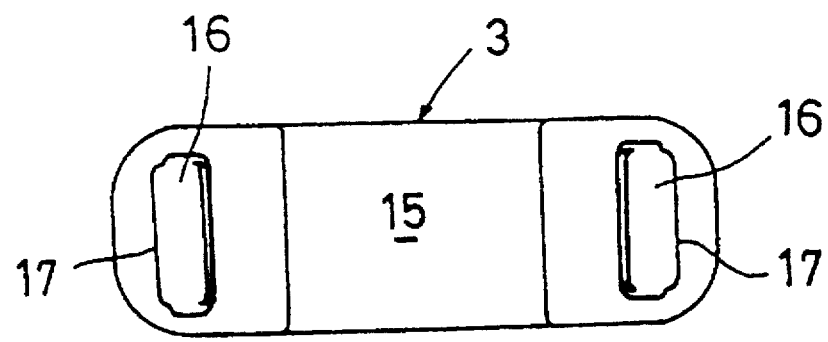
FIG. 7 is a rear view of FIG. 5.
Figure 8:
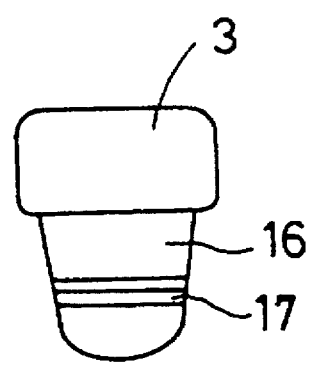
FIG. 8 is a right side view of FIG. 6.

Referring to FIG. 1, goggles 1 comprise a pair of right and left eyecups 2,2, a connecting member 3 in the form of a strap interconnecting the eyecups 2,2, and an elastic band 4 having opposite ends each connected to an outer end of each eyecup 2.

The elastic band 4 is secured to the eyecups 2,2 with band stoppers 5,5.

As shown in FIGS. 1 to 4, the eyecup 2 is integrally molded of a synthetic resin such as a transparent or translucent polycarbonate and comprises a flat lens portion 6 on the front side thereof and a peripheral wall 7 rearwardly extending from the peripheral edge of the lens portion 6. The rear end of the peripheral wall 7 is provided with a pad receiving portion 8 for receiving a soft and elastic annular pad (not shown). The peripheral wall 7 is provided with a mount portion 9 projecting from the nasal or inner side thereof for connecting to the connecting member 3, and a band connecting portion 10 for securing one end of the elastic band 4 at the outer end of the peripheral wall.

On the front side of the mount portion 9 of the eyecup 2 is formed a flat surface 11 which is substantially rectangular and extends generally parallel to the lens portion 6. The mount portion 9 defines a plurality (two in this embodiment) of substantially rectangular engagement holes 12 which extend through the mount portion 9 in the thicknesswise direction and are aligned in the longitudinal direction of the eyecup 2. The engagement holes 12 are each in the form of a vertically elongated rectangle.

The band connecting portion 10 has a recess 13 formed from the front side thereof and a band insertion hole 14 in the rear wall of the recess 13. Into the recess 13 is securely fitted the band stopper 5.

As shown in FIGS. 5 to 8, the connecting member 3 is of a substantially rectangular shape elongated transversely in the front view of the goggles and is formed of a synthetic resin such as a nylon elastomer. The connecting member 3 has, on the rear side thereof, a recess 15 in a longitudinally central portion thereof so as not to contact the nose of a user. Further, the connecting member 3 has, on opposite sides of the recess 15, contact surfaces 15a closely contacting the corresponding flat surfaces 11. Each contact surface 15a is provided with an engaging claw 16 protruding therefrom. The engaging claw 16 includes a base portion having substantially the same cross sectional configuration as the engagement hole 12 so as to be closely fitted into the hole 12.

The engaging claw 16 has an engaging protuberance 17 on the outer side thereof so that the protuberance 17 hooks the rear peripheral edge of the engagement hole 12 of the eyecup 2. The engaging protuberance 17 is formed by offsetting the axis of the tip portion of the claw 16 with respect to that of the base portion thereof. The engaging claw 16 is elastically deformable.

The vertical width of the connecting member 3, when viewed in the front view of the goggles, is substantially equal to that of the mount portion 9 of the eyecup 2.

In wearing the aforementioned embodiment, the user selects one of the engagement holes 12 in the mount portion of each eyecup 2 and inserts the engaging claw 16 of the connecting member 3 into the selected hole 12. When the claw 16 passes through the selected hole 12, the engaging protuberance 17 of the claw 16 hooks the rear peripheral edge of the hole 12, thus preventing the claw 16 from coming off the hole 12. In this way the goggles of present invention allows the user to interconnect the eyecups 2,2 through the connecting member 3 with facilitated operations and provides a good fit onto the wearing portion or the face of the user.

Since the engaging claw 16 is tightly fitted into the engagement hole 12 while at the same time the flat surface 11 and the contact surface 15a are closely contacted with each other, the connecting member 3 and the mount portion 9 are unlikely to be relatively displaced. Therefore, the pair of right and left eyecups 2 will hardly be displaced, resulting in improved fit onto the face of a user.

In changing the position of the engaging claw 18 of the connecting member 3, the claw 18 can readily drawn out of the engagement hole 12 by pressing the outer side of the engaging protuberance 17 on the rear side of the mount portion 9 with a finger to elastically deform the claw 18, releasing the engagement between the engaging protuberances 17 and the peripheral edge of the engagement hole 12 and drawing the connecting member 3 forward. Subsequently, the user selects another engagement hole 12 and inserting the claw 18 into the selected hole 12. Thus, the goggles can be readjusted with ease.

The embodiment having been described in the present specification is not limitative but only illustrative of the invention, and may be subjected to any change of design. For example, each mount portion 9 may be provided with more than two engagement holes 12 and may be shaped differently within design choice. The present invention may be applied to goggles not only for swimming but also for skiing, motorcycling and the like.

What is claimed is:

1. Goggles comprising a pair of right and left eyecups, a connecting member interconnecting opposing inner ends of the eyecups, and an elastic band having opposite ends each connected to another end of each of the eyecups, wherein said eyecups are each provided with a mount portion which defines a plurality of engagement holes aligned longitudinally of the eyecups, and said connecting member is removably fitted into one of said plurality of engagement holes of each mount portion selectively.

2. Goggles as set forth in claim 1, wherein said eyecups each comprise a lens portion and a peripheral wall rearwardly extending from a peripheral edge of the lens portion, said mount portion projects from the peripheral wall substantially parallel to the lens portion and has a front side comprising a flat surface, and said engagement holes are in the form of vertically elongated slits.

3. Goggles as set forth in claim 2, wherein said connecting member is of a rectangular shape transversely elongated in a front view of the goggles and has a rear side formed with a recess in a longitudinally central portion thereof and contact surfaces on opposite sides of the recess which closely contact the corresponding flat surfaces of the eyecups, and said contact surfaces are each formed with an engaging claw protruding rearwardly therefrom and removably inserted into one of said engagement holes.

4. Goggles as set forth in claim 3, wherein said engaging claw has an engaging protuberance on a tip portion thereof which hooks a peripheral edge of said one of the engagement holes.

5. Goggles as set forth in claim 4, wherein said engaging claw has a base portion having substantially the same cross sectional configuration as each of said engagement holes and closely fitted into said one of the engagement holes, said engaging protuberance is formed by offsetting the axis of said tip portion of the claw with respect to that of the base portion of the claw.

6. Goggles as set forth in claim 5, wherein said engaging claw is elastically deformable.

7. Goggles comprising:
- a left eyecup having a first inner end and a second opposite end, the first inner end of the left eyecup having a left mount portion, the left mount portion having a plurality of engagement holes;
- a right eyecup having a first inner end and a second opposite end, the first inner end of the right eyecup having a right mount portion, the right mount portion having a plurality of engagement holes;
- a connecting member, removably connected to one of the plurality of engagement holes in the left mount portion of the left eyecup and to one of the plurality of engagement holes in the right mount portion of the right eyecup, so that the left and right eyecups are interconnected; and
- an elastic band having a first end and a second end, the first end of the elastic band connected to the second opposite end of the left eyecup and the second end of the elastic band connected to the second opposite end of the right eyecup.

* * * * *